US010611807B2

(12) United States Patent
McGrath et al.

(10) Patent No.: US 10,611,807 B2
(45) Date of Patent: Apr. 7, 2020

(54) PROMOTERS SUITABLE FOR HETEROLOGOUS GENE EXPRESSION IN YEAST

(71) Applicants: DSM IP ASSETS B.V., Heerlen (NL); Jessica Leigh McGrath, Cambridge, MA (US); Bastien Chevreux, Rheinfelden (DE); Peter Scott Yorgey, Cambridge, MA (US)

(72) Inventors: Jessica Leigh McGrath, Cambridge, MA (US); Bastien Chevreux, Rheinfelden (DE); Peter Scott Yorgey, Cambridge, MA (US)

(73) Assignee: DSM IP ASSETS B.V., Heerlen (NL)

( * ) Notice: Subject to any disclaimer, the term of this patent is extended or adjusted under 35 U.S.C. 154(b) by 9 days.

(21) Appl. No.: 15/112,911

(22) PCT Filed: Jan. 29, 2015

(86) PCT No.: PCT/US2015/013453
§ 371 (c)(1),
(2) Date: Jul. 20, 2016

(87) PCT Pub. No.: WO2015/116781
PCT Pub. Date: Aug. 6, 2015

(65) Prior Publication Data

US 2016/0333058 A1 Nov. 17, 2016

Related U.S. Application Data

(60) Provisional application No. 61/933,979, filed on Jan. 31, 2014.

(51) Int. Cl.

| | |
|---|---|
| ***C07K 14/39*** | (2006.01) |
| ***C12N 15/63*** | (2006.01) |
| ***C12P 23/00*** | (2006.01) |
| ***C12N 15/74*** | (2006.01) |
| ***C12P 1/02*** | (2006.01) |
| ***C12N 15/81*** | (2006.01) |
| ***C12P 21/02*** | (2006.01) |

(52) U.S. Cl.
CPC ............ *C07K 14/39* (2013.01); *C12N 15/815* (2013.01); *C12P 1/02* (2013.01); *C12P 21/02* (2013.01); *C12P 23/00* (2013.01)

(58) Field of Classification Search
None
See application file for complete search history.

(56) References Cited

U.S. PATENT DOCUMENTS

| | | | |
|---|---|---|---|
| 6,110,703 | A | 8/2000 | Egel-Mitani et al. |
| 2006/0110806 | A1 | 5/2006 | Damude et al. |
| 2006/0115881 | A1 | 6/2006 | Damude et al. |

FOREIGN PATENT DOCUMENTS

| | | | |
|---|---|---|---|
| EP | 0220864 | A1 | 5/1987 |
| EP | 0220864 | A | 6/1987 |
| WO | WO1997044470 | | 11/1997 |
| WO | WO 1997044470 | A1 | 11/1997 |
| WO | WO 2004104180 | A3 | 12/2004 |
| WO | WO 2006102342 | A2 | 9/2006 |
| WO | WO2006102432 | A2 | 9/2006 |
| WO | WO 2006102432 | A2 | 9/2006 |
| WO | WO2008042338 | A2 | 4/2008 |
| WO | WO 2008042338 | A2 | 4/2008 |
| WO | WO 2008073367 | A1 | 6/2008 |
| WO | WO 2016055578 | A1 | 4/2016 |

OTHER PUBLICATIONS

Sequence Alignment of SEQ ID No. 1 with CR382130. Search conducted on Jan. 10, 2018, 6 pages.*

Sequence Alignment of SEQ ID No. 2 with CR382130. Search conducted on Jan. 10, 2018, 6 pages.*

J. Sambrook, Molcular Cloning, A Laboratory Manual, 1989, Table of contents, Second.

John Wiley & Sons, Biochemical Pathways, An Atlas of Biochemistry and Molecular Biology, 1999, (Book).

John Wiley & Sons, Current Protocols in Molecular Biology, 1989, 6.3.1-6.3.6 (Book).

Obtained From Internet, *Yarrowia lipolytica* CLIB122 Chromosome D Complete Sequence, 2015, www.ncbi.nlm.nih.gov/nucleotide/49648093?report=genbank&log$=nuclalign&blast_rank=1&RID=JZWFZZTB016.

Ogrydziak et al., Alkaline Extracellular Protease Produced by *Saccharomycopsis lipolytica*, 1982, 1225-1234, 128.

Ogrydziak et al., Regulation of Extracellular Protease Production in *Candida lipolytica*, Biochimica et, 1977, 525-538, 497.

Ong et al., Nutrition, Lipids, Health and Disease, Proceedings of the UNESCO, 1995, (Book).

Voet et al., Biochemistry, 1995, Abstract.

Weinheim et al., Ullmann's Encyclopedia of Industrial Chemistry, Vitamins, 1996, 443-613, A27.

Blazeck, J., et al., "Generalizing a hybrid synthetic promoter approach in *Yarrowia lipolytica*," Appl Microbiol Biotechnol 97: 3037-3052 (2012).

Dujon, B., et al., "*Yarrowia lipolytica* CLIB122 chromosome D complete sequence," (2015).

Madzak, C., et al., "Heterologous protein expression and secretion in the non-conventional yeast *Yarrowia lipolytica*: a review," Journal of Biotechnology 109, 63-81 (2004).

(Continued)

*Primary Examiner* — Channing S Mahatan
(74) *Attorney, Agent, or Firm* — Nixon & Vanderhye P.C.

(57) ABSTRACT

The present invention relates to the use of novel promoters for heterologous gene expression, preferably for expression of genes in organisms of the genus *Yarrowia*, to the genetically modified organisms of the genus *Yarrowia*, and to a process for producing biosynthetic products by cultivating the genetically modified organisms.

14 Claims, 3 Drawing Sheets

Specification includes a Sequence Listing.

(56) References Cited

OTHER PUBLICATIONS

Madzak, C., *Yarrowia lipolytica*: recent achievements in heterologous protein expression and pathway engineering, Appl Microbiol Biotechnol 99: 4559-4577 (2015).

Matthäus, F., et al., "Production of Lycopene in the Non-Carotenoid-Producing Yeast *Yarrowia lioplytica*," Applied and Environmental Microbiology, vol. 80, No. 5, 1660-1669 (2013).

Ogrydziak, D., et al., "Alkaline Extracellular Protease Produced by *Saccharomycopsis lipolytica* CX161-1B," Journal of General Microbiology 128, 1225-1234 (1982).

Ogrydziak, D., et al., "Regulation of Extracellular Protease Production in *Candida lipolytica*," Biochimica et Biophysica Acta, 497: 525-538 (1977).

Shuliang et al., "One-step integration of multiple genes into the oleaginous yeast *Yarrowia lipolytica*," Biotechnology Letters, vol. 36, Issue 12, 2523-2528 (2014).

* cited by examiner

SEQUENCE LISTING

<160> NUMBER OF SEQ ID NOS: 16

<210> SEQ ID NO 1
<211> LENGTH: 1002
<212> TYPE: DNA
<213> ORGANISM: Yarrowia lipolytica

<400> SEQUENCE: 1

```
tagtgcaatc acatgttgct actgtacctg ctgtggacca cgcacggcgg aacgtaccgt      60

acaaatattt tcttgctcac atgactctct ctcggccgcg cacgccggtg gcaaattgct     120

cttgcattgg ctctgtctct agacgtccaa accgtccaaa gtggcagggt gacgtgatgc     180

gacgcacgaa ggagatggcc cggtggcgag gaaccggaca cggcgagccg gcgggaaaaa     240

aggcggaaaa cgaaaagcga agggcacaat ctgacggtgc ggctgccacc aacccaagga     300

ggctattttg ggtcgctttc catttcacat tcgccctcaa tggccacttt gcggtggtga     360

acatggtttc tgaaacaacc ccccagaatt agagtatatt gatgtgttta agattgggtt     420

gctatttggc cattgtgggg gagggtagcg acgtggagga cattccaggg cgaattgagc     480

ctagaaagtg gtaccattcc aaccgtctca gtcgtccgaa ttgatcgcta taactatcac     540

ctctctcaca tgtctacttc cccaaccaac atccccaacc tcccccacac taaagttcac     600

gccaataatg taggcactct ttctgggtgt gggacagcag agcaatacgg aggggagatt     660

acacaacgag ccacaattgg ggagatggta gccatctcac tcgacccgtc gacttttggc     720

aacgctcaat tacccaccaa atttgggctg gagttgaggg gaccgtgttc cagcgctgta     780

ggaccagcaa cacacacggt atcaacagca accaacgccc ccgctaatgc acccagtact     840

gcgcaggtgt gggccaggtg cgttccagat gcgagttggc gaaccctaag ccgacagtgt     900

actttttggg acgggcagta gcaatcgtgg gcggagaccc cggtgtatat aaaggggtgg     960

agaggacgga ttattagcac caacacacac acttatacta ca                       1002
```

<210> SEQ ID NO 2
<211> LENGTH: 995
<212> TYPE: DNA
<213> ORGANISM: Yarrowia lipolytica

<400> SEQUENCE: 2

```
tcgcggtcag aaggggcagc tctaaacgaa gaactgcggt caggtgacac aactttttcc      60

atctcagggt gtgtcgcgtg tgcttcatcc aaactttagt tggggttcgg gttcgcgcga     120

gatgatcacg tgccctgatt tggtgtcgtc cccgtcgcg ctgcgcacgt gatttattta     180

tttccggtgg ctgctgtcta cgcggggcct tctctgccct tctgtttcaa ccttcgggcg     240

gttctcgtaa ccagcagtag caatccattt cgaaactcaa agagctaaaa acgttaaacc     300

tcagcagtcg ctcgacgaat gggctgcggt tgggaagccc acgaggccta tagccagagc     360

ctcgagttga caggagccca gacgcctttt ccaacggcaa cttttatata aaatggcaat     420

gtattcatgc aattgcggcc gtgtcaggtt ggagacactg gaccacactc tccattgctt     480

cctgaggaga tggatcattg ctagtgcatc tacgcgcagc aatcccgcaa gctcgacaac     540

cgtagatggg ctttggtggg ccaatcaatt acgcaacccg cacgttaaat tgtatgagga     600

aggaaggcca cggtacaaag tgggtggtct tcacccagtg gttgttggtg gcgtcatgca     660

gaccatgcat tggggatagc acagggttgg ggtgtcttgt ggactcaatg ggtgaaagga     720

gatggaaaag ggcggtgaaa agtggtagaa tcgaaatccc tgacgtcaat ttataaagta     780

aaatgcgttt ctgccatttt gctcccctcc ttctttcgca atcgcctccc caaaagttgt     840
```

cgtggcagta cacatgcttg catacaatga agctaatccg gcttgctcag tagttgctat 900
atccaggcat ggtgtgaaac ccctcaaagt atatatagga gcggtgagcc ccagtctggg 960
gtcttttctc tccatctcaa aactactttc tcaca 995

<210> SEQ ID NO 3
<211> LENGTH: 43
<212> TYPE: DNA
<213> ORGANISM: Artificial Sequence
<220> FEATURE:
<223> OTHER INFORMATION: MO8250, sequence used to amplify SEQ ID NO:1

<400> SEQUENCE: 3
cacacaaagc ttggtaccag atagtgcaat cacatgttgc tac 43

<210> SEQ ID NO 4
<211> LENGTH: 43
<212> TYPE: DNA
<213> ORGANISM: Artificial Sequence
<220> FEATURE:
<223> OTHER INFORMATION: MO8251, sequence used to amplify SEQ ID NO:1

<400> SEQUENCE: 4
cacacatttt gtggctagca tgtagtataa gtgtgtgtgt tgg 43

<210> SEQ ID NO 5
<211> LENGTH: 40
<212> TYPE: DNA
<213> ORGANISM: Artificial Sequence
<220> FEATURE:
<223> OTHER INFORMATION: MO8254, sequence used to amplify SEQ ID NO:2

<400> SEQUENCE: 5
cacacaaagc ttggtaccag atcgcggtca gaaggggcag 40

<210> SEQ ID NO 6
<211> LENGTH: 44
<212> TYPE: DNA
<213> ORGANISM: Artificial Sequence
<220> FEATURE:
<223> OTHER INFORMATION: MO8255, sequence used to amplify SEQ ID NO:2

<400> SEQUENCE: 6
cacacatttt gtggctagca tgtgagaaag tagttttgag atgg 44

<210> SEQ ID NO 7
<211> LENGTH: 24
<212> TYPE: DNA
<213> ORGANISM: Artificial Sequence
<220> FEATURE:
<223> OTHER INFORMATION: MO7492, forward primer sequence

<400> SEQUENCE: 7
acgttgtgcc catctactct ggtt 24

<210> SEQ ID NO 8
<211> LENGTH: 24
<212> TYPE: DNA
<213> ORGANISM: Artificial Sequence
<220> FEATURE:
<223> OTHER INFORMATION: MO7493, reverse primer sequence

<400> SEQUENCE: 8
tcggcggagt tggtgaaaga gtaa 24

```
<210> SEQ ID NO 9
<211> LENGTH: 24
<212> TYPE: DNA
<213> ORGANISM: Artificial Sequence
<220> FEATURE:
<223> OTHER INFORMATION: MO7714, forward primer sequence

<400> SEQUENCE: 9

agtgcggtgg tatcgataag cgaa                                            24


<210> SEQ ID NO 10
<211> LENGTH: 24
<212> TYPE: DNA
<213> ORGANISM: Artificial Sequence
<220> FEATURE:
<223> OTHER INFORMATION: MO76, reverse primer sequence

<400> SEQUENCE: 10

tctcgctcag ccttaagctt gtca                                            24


<210> SEQ ID NO 11
<211> LENGTH: 24
<212> TYPE: DNA
<213> ORGANISM: Artificial Sequence
<220> FEATURE:
<223> OTHER INFORMATION: MO8241, forward primer sequence

<400> SEQUENCE: 11

acatctccga cgagaagaac aagc                                            24


<210> SEQ ID NO 12
<211> LENGTH: 24
<212> TYPE: DNA
<213> ORGANISM: Artificial Sequence
<220> FEATURE:
<223> OTHER INFORMATION: MO8242, reverse primer sequence

<400> SEQUENCE: 12

agttgttgat ggactccttg gcct                                            24


<210> SEQ ID NO 13
<211> LENGTH: 24
<212> TYPE: DNA
<213> ORGANISM: Artificial Sequence
<220> FEATURE:
<223> OTHER INFORMATION: MO8239, forward primer sequence

<400> SEQUENCE: 13

agtttgcccg acagaaggag aaca                                            24


<210> SEQ ID NO 14
<211> LENGTH: 24
<212> TYPE: DNA
<213> ORGANISM: Artificial Sequence
<220> FEATURE:
<223> OTHER INFORMATION: MO8240, reverse primer sequence

<400> SEQUENCE: 14

atggagttga cggcgaagat gaga                                            24


<210> SEQ ID NO 15
<211> LENGTH: 24
<212> TYPE: DNA
<213> ORGANISM: Artificial Sequence
<220> FEATURE:
<223> OTHER INFORMATION: MO7655, forward primer sequence
```

-continued

```
<400> SEQUENCE: 15

aggctacctt aagcggcttt acca                                          24


<210> SEQ ID NO 16
<211> LENGTH: 24
<212> TYPE: DNA
<213> ORGANISM: Artificial Sequence
<220> FEATURE:
<223> OTHER INFORMATION: MO7656, reverse primer sequence

<400> SEQUENCE: 16

ttccggctta gctgcgtaga gaaa                                          24
```

PROMOTERS SUITABLE FOR HETEROLOGOUS GENE EXPRESSION IN YEAST

CROSS-REFERENCE TO RELATED APPLICATIONS

This application claims the benefit of the filing date of U.S. Provisional Patent Application No. 61/933,979 filed Jan. 31, 2014, the disclosure of which is hereby incorporated herein by reference.

FIELD OF INVENTION

The present invention relates to the use of novel promoters for heterologous gene expression, preferably for expression of genes in organisms of the genus *Yarrowia*, to the genetically modified organisms of the genus *Yarrowia*, and to a process for producing biosynthetic products by cultivating the genetically modified organisms.

BACKGROUND OF THE INVENTION

Various biosynthetic products, for example, fine chemicals, such as, inter alia, amino acids, vitamins, carotenoids, but also proteins, are produced by natural metabolic processes in cells and used in various branches of industry, including the human and animal food, cosmetics, and pharmaceutical industries.

Production thereof on a large scale takes place in part by means of biotechnological processes using microorganisms which have been developed in order to produce and secrete large amounts of the particular desired substance.

For example, carotenoids are synthesized de novo in bacteria, algae and fungi. In recent years there have been increasing attempts to utilize oleaginous yeast and fungi as organisms for producing fine chemicals, especially for producing vitamins and carotenoids.

Carotenoids, such as lutein, zeaxanthin, astaxanthin and beta carotene, are extracted for example from *Yarrowia* as so-called oleoresin. These oleoresins are used both as constituents of dietary supplements and in the feed sector.

Ketocarotenoids, meaning carotenoids which comprise at least one keto group, such as, for example, astaxanthin, canthaxanthin, echinenone, 3-hydroxyechinenone, 3'-hydroxyechinenone, adonirubin and adonixanthin, are natural antioxidants and pigments which are produced by some algae, organisms and microorganisms as secondary metabolites.

Biosynthesis of these molecules in organisms which is able to produce them, such as yeast and bacteria, has been characterized in details (Weinheim et al., (1996) Ullmann's Encyclopedia of Industrial Chemistry, "Vitamins", Vol. A27, pp. 443-613; Biochemical Pathways: An Atlas of Biochemistry and Molecular Biology, John Wiley & Sons, Michal, G. Ed. (1999); Ong, A. S., Niki, E. and Packer, L., (1995) "Nutrition, Lipids, Health and Disease" Proceedings of the UNESCO/Confederation of Scientific and Technological Associations in Malaysia and the Society for Rree Radical Research-Asia, held on Sep. 1-3, 1994, in Penang, Malaysia, AOCS Press, Champaign, Ill. X, 374 S). In particular, biosynthesis of carotenoids in *Yarrowia* is described in WO2006/102342.

Owing to their coloring properties, the ketocarotenoids and especially astaxanthin are used as pigmenting agents in livestock nutrition, especially in the rearing of trout, salmon and shrimps.

An economical biotechnological process for producing natural biosynthetic products and especially carotenoids is therefore of great importance.

WO 2008/042338 discloses a number of promoters used for overexpression of carotenoid biosynthesis genes in *Yarrowia*.

One type of promoters is disclosed in EP 0220864 A. This publication describes a *Yarrowia lipolytica* yeast promoter XPR2. The XPR2 yeast promoter is only active at pH above 6.0 on media lacking preferred carbon and nitrogen sources and full induction requires high levels of peptone in the culture medium (Ogrydziak, D. M., Demain, A. L., and Tannenbaum, S. R., (1977) Biochim. Biophys. Acta. 497: 525-538; Ogrydziak, D. M. and Scharf, S. J., (1982) Gen. Microbiol. 128: 1225-1234.)

Another type of promoters for expressing genes in yeast, as for example *Yarrowia*, is described in WO 1997/044470.

The promoters used to date cannot, however, fully satisfy the requirement for high expression in *Yarrowia*. There was consequently a need to provide promoters which better satisfy the requirements.

Therefore, an object of the present invention is to provide new improved yeast promoters, especially for use in expression cloning in yeast, but also for heterologous expression of desired fine chemicals as defined above in an expression system of choice.

SUMMARY OF THE INVENTION

The present invention is directed to a recombinant nucleic acid molecule comprising: a) polynucleotide sequence having at least 90% identity to the polynucleotide sequence of SEQ ID NO:1 (referred to herein as HSP) or SEQ ID NO:2 (referred to herein as HYP), or b) nucleic acid sequence which hybridizes with the nucleic acid sequence SEQ ID NO:1 or SEQ ID NO:2 under stringent conditions, or c) functionally equivalent fragments of the sequences under a) or b).

In one aspect, the invention is directed to a recombinant nucleic acid molecule comprising a polynucleotide sequence having at least 95% identity to the polynucleotide sequence of SEQ ID NO:1 or SEQ ID NO:2.

In a specific aspect of the invention, the recombinant nucleic acid molecule functions as a promoter. The recombinant nucleic acid molecule is used for regulating the expression of a gene in yeast. In one embodiment, the yeast is an organism of the genus *Yarrowia*. In one embodiment, the yeast is a strain of *Yarrowia lipolytica*. In another embodiment, the gene being regulated is heterologous to an organism of the genus *Yarrowia*.

In one embodiment, the recombinant nucleic acid molecule is functionally linked to a gene encoding a protein. In an embodiment, the gene is functionally linked to one or more other regulatory signals. In a specific embodiment, the functionally linked gene is selected from the group of nucleic acids encoding a protein from: a) the biosynthetic pathway of organic acids, or b) the biosynthetic pathway of lipids and fatty acids, or c) the biosynthetic pathway of diols, or d) the biosynthetic pathway of aromatic compounds, or e) the biosynthetic pathway of vitamins, or f) the biosynthetic pathway of carotenoids, especially ketocarotenoids.

In one embodiment, the recombinant nucleic acid molecule described in this invention is a vector.

The present invention also relates to a genetically modified microorganism comprising the above-described recombinant nucleic acid molecule. In one embodiment, the microorganism is a member of the genus *Yarrowia*. In another embodiment, the above-described recombinant nucleic acid molecule is used for the expression of one or more genes in the host microorganism, wherein the expression rate of the at least one or more genes is increased as compared with the wild type. In a specific embodiment, the regulation of the expression of the gene in the host microorganism is achieved by: a) introducing one or more of the above-described recombinant nucleic acid molecule into the genome of the host microorganism, so that expression of one or more endogenous genes of the host microorganism takes place under the control of the introduced recombinant nucleic acid molecule; b) introducing one or more genes into the genome of the host microorganism, so that the expression of one or more of the introduced genes takes place under the control of the above-described recombinant nucleic acid molecule which is endogenous to the host microorganism; or c) introducing one or more nucleic acid constructs into the host microorganism, wherein said one or more nucleic acid constructs comprise at least one of the above-described recombinant nucleic acid molecule and the recombinant nucleic acid molecule is functionally linked to one or more genes to be expressed.

The present invention also relates to a process for production of a biosynthetic product, comprising the steps of: a) cultivating a genetically modified microorganism of the genus *Yarrowia* in a medium, wherein the genetically modified microorganism comprises the above-described recombinant nucleic acid molecule, wherein the recombinant nucleic acid molecule is functionally linked to a gene encoding a protein; and b) producing the biosynthetic product made in step a). In some embodiments, the biosynthetic product is secreted into the medium. In other embodiments, the biosynthetic product accumulates within the microorganism. In some embodiments, the biosynthetic product is recovered from an isolated microbial biomass. In some embodiments, the biosynthetic product is carotenoids.

SEQUENCE LISTING

Figure 1:
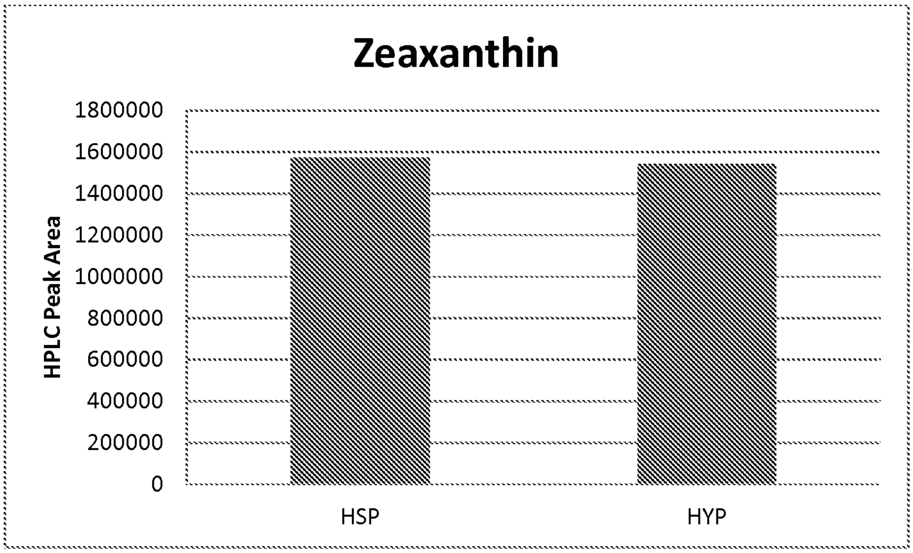
FIG. 1 and FIG. 2 show the average zeaxanthin and astaxanthin levels, respectively, as HPLC peak areas, for the two promoters tested in shake flask experiments (for zeaxanthin: 10 transformants having HSP promoter were averaged, and 5 transformants having HYP promoter were averaged. For astaxanthin production: 12 transformants having HSP promoter were averaged, and 12 transformants having HYP promoter were averaged).

The nucleic acid sequences listed in the accompanying sequence listing are shown using standard letter abbreviation for nucleotide bases as defined in 37 C.F.R. § 1.822. Only one strand of each nucleic acid sequence is shown, but the complementary strand is understood to be included by any reference to the displayed strand. In the accompanying sequence listing:

SEQ ID NO: 1 shows the HSP promoter from *Yarrowia lipolytica*.

tagtgcaatc acatgttgct actgtacctg ctgtggacca
cgcacggcgg aacgtaccgt acaaalattt tcttgctcac
atgactctct ctcggccgcg cacgccggtg gcaaattgct
cttgcattgg ctctgtctct agacgtccaa accgtccaaa
gtggcagggt gacgtgatgc gacgcacgaa ggagatggcc
cggtggcgag gaaccggaca cggcgagccg gcgggaaaaa
aggcggaaaa cgaaaagcga agggcacaat ctgacggtgc
ggctgccacc aacccaagga ggctattttg ggtcgctttc
catttcacat tcgccctcaa tggccacttt gcggtggtga
acatggtttc tgaaacaacc ccccagaatt agagtatatt
gatgtgttta agattgggtt gctatttggc cattgtgggg
gagggtagcg acgtggagga cattccaggg cgaattgagc
ctagaaagtg gtaccattcc aaccgtctca gtcgtccgaa
ttgatcgcta taactatcac ctctctcaca tgtctacttc
cccaaccaac atccccaacc tcccccacac taaagttcac
gccaataatg taggcactct ttctgggtgt gggacagcag
agcaatacgg aggggagatt acacaacgag ccacaattgg
ggagatggta gccatctcac tcgacccgtc gacttttggc
aacgctcaat tacccaccaa atttgggctg gagttgaggg
gaccgtgttc cagcgctgta ggaccagcaa cacacacggt
atcaacagca accaacgccc ccgctaatgc acccagtact
gcgcaggtgt gggccaggtg cgttccagat gcgagttggc
gaaccctaag ccgacagtgt actttttggg acgggcagta
gcaatcgtgg gcggagaccc cggtgtatat aaaggggtgg
agaggacgga ttattagcac caacacacac acttatacta ca SEQ ID NO: 2 shows the HYP promoter from *Yarrowia lipolytica*.

tcgcggtcag aaggggcagc tctaaacgaa gaactgcggt
caggtgacac aactttttcc atctcagggt gtgtcgcgtg
tgcttcatcc aaactttagt tggggttcgg gttcgcgcga
galgatcacg tgccctgatt tggtgtcgtc ccccgtcgcg
ctgcgcacgt gatttattta tttccggtgg ctgctgtcta
cgcggggcct tctctgccct tctgtttcaa ccttcgggcg
gltctcgtaa ccagcagtag caatccattt cgaaactcaa
agagctaaaa acgttaaacc tcagcagtcg ctcgacgaat
gggctgcggt tgggaagccc acgaggccta tagccagagc
ctcgagttga caggagccca gacgcctttt ccaacggcaa
cttttatata aaatggcaat gtattcatgc aattgcggcc
gtgtcaggtt ggagacactg gaccacactc tccattgctt
cctgaggaga tggatcattg ctagtgcatc tacgcgcagc
aatcccgcaa gctcgacaac cgtagatggg ctttggtggg -continued

```
ccaatcaatt acgcaacccg cacgttaaat tgtatgagga

aggaaggcca cggtacaaag tgggtggtct tcacccagtg

gttgttggtg gcgtcatgca gaccatgcat tggggatagc

acagggttgg ggtgtcttgt ggactcaatg ggtgaaagga

gatggaaaag ggcggtgaaa agtggtagaa tcgaaatccc

tgacgtcaat ttataaagta aaatgcgttt ctgccatttt

gctcccctcc ttctttcgca atcgcctccc caaaagttgt

cgtggcagta cacatgcttg catacaatga agctaatccg

gcttgctcag tagttgctat atccaggcat ggtgtgaaac

ccctcaaagt atatatagga gcggtgagcc ccagtctggg

gtcttttctc tccatctcaa aactactttc tcaca
```

DETAILED DESCRIPTION OF THE INVENTION

The present invention is directed to novel recombinant nucleic acid molecules that are promoters. A promoter of the invention is a region of DNA that directs transcription of an associated coding region (gene).

The recombinant nucleic acid molecule according to the present invention comprises: a) polynucleotide sequence having at least 90% identity to the polynucleotide sequence of SEQ ID NO:1 or SEQ ID NO:2, or b) nucleic acid sequence which hybridizes with the nucleic acid sequence SEQ ID NO:1 or SEQ ID NO:2 under stringent conditions, or c) functionally equivalent fragments of the sequences under a) or b).

Particularly preferred recombinant nucleic acid molecules have an identity of at least 70%, preferably at least 80%, at least 85%, at least 90%, at least 92%, at least 95%, at least 96%, at least 97%, at least 98%, particularly preferably at least 99%, with the respective nucleic acid sequence SEQ ID NO: 1 or 2. The percentage identity can be found over a sequence of at least 100, at least 200, at least 300, at least 400, at least 500, at least 800 nucleotides, or over the entire sequence of the nucleic acid sequence of SEQ ID NO:1 or SEQ ID NO:2.

In some embodiments, the above-mentioned homologues of SEQ ID NO:1 or SEQ ID NO:2 are derived from polynucleotide sequence of SEQ ID NO:1 or SEQ ID NO:2 by substitution, insertion or deletion of nucleotides.

The invention also relates to recombinant nucleic acid molecules comprising a nucleic acid sequence which hybridizes with the nucleic acid sequence of SEQ ID No:1 or SEQ ID NO:2 under stringent conditions.

In one aspect, the invention relates to a recombinant nucleic acid molecule as shown in SEQ ID NO:1 or SEQ ID NO:2, or nucleic acid sequence which hybridizes with the nucleic acid sequence SEQ ID NO:1 or SEQ ID NO:2 under stringent conditions, or functionally equivalent fragments of the sequences above, wherein recombinant nucleic acid molecule functions as a promoter.

The nucleic acid sequences SEQ ID NO:1 and SEQ ID NO:2 each represents a promoter sequence cloned from *Yarrowia lipolytica.*

In some embodiments, the promoter can be used in regulating the expression of a gene in yeast including, but not limited to the genus *Yarrowia*. In a specific embodiment, the promoter can be used in regulating the expression of a gene in a strain of *Yarrowia lipolytica.*

A promoter of the invention can have promoter activity at least in a yeast, and includes full-length promoter sequences and functional fragments thereof, fusion sequences, and homologues of a naturally occurring promoter. Restriction enzymes can be used to digest the nucleic acid molecules of the invention, followed by the appropriate assay to determine the minimal sequence required for promoter activity. Such fragments themselves individually represent embodiments of the present invention. A homologue of a promoter differs from a naturally occurring promoter in that at least one, two, three, or several, nucleotides have been deleted, inserted, inverted, substituted and/or derivatized. A homologue of a promoter can retain activity as a promoter, at least in a yeast, although the activity can be increased, decreased, or made dependent upon certain stimuli. The promoters of the invention can comprise one or more sequence elements that confer developmental and regulatory control of expression.

It has been found that the two new promoters (HSP and HYP promoters, illustrated by SEQ ID NO:1 and SEQ ID NO:2, respectively) and their homologues are particularly suitable for enhancing the expression of a target gene in yeast, in particular in *Yarrowia*, to a relatively high level. Examples of the target gene include the genes involved in the pathway of making carotenoids and other isoprenoids. In some embodiment, the HSP and HYP promoters including their homologues can cause the accumulation of carotenoids in a relatively high concentration.

In preferred embodiments the present invention provides two cloned yeast promoters (HSP and HYP promoters, respectively).

A cloned yeast promoter refers to a yeast promoter cloned by standard cloning procedure used in genetic engineering to relocate a segment of DNA from its natural location to a different site where it will be reproduced. The cloning process involves excision and isolation of the desired DNA segment, insertion of the piece of DNA into the vector molecule and incorporation of the recombinant vector into a cell where multiple copies or clones of the DNA segment will be replicated.

The yeast promoter DNA sequence of the invention may be isolated from a *Yarrowia lipolytica* yeast strain. Alternatively, the promoter sequence of the invention may be constructed on the basis of the DNA sequence presented as DNA sequence shown in SEQ ID NO: 1 or SEQ ID NO: 2.

Yeast promoter refers to the nucleotide sequence(s) at the 5' end of a structural gene which direct(s) the initiation of transcription. The promoter sequence is to drive the expression of a downstream gene. The promoter drives transcription by providing binding sites to RNA polymerases and other initiation and activation factors. Usually the promoter drives transcription preferentially in the downstream direction. The level of transcription is regulated by the promoter. Thus, in the construction of heterologous promoter/structural gene combinations, the structural gene is placed under the regulatory control of a promoter such that the expression of the gene is controlled by the promoter sequence(s). The promoter is positioned preferentially upstream to the structural gene and at a distance from the transcription start site that approximates the distance between the promoter and the gene it controls in its natural setting. As it is known in the art, some variation in this distance can be tolerated without loss of promoter function.

The transcription efficiency of the promoter may, for instance, be determined by a direct measurement of the amount of mRNA transcription from the promoter, e.g., by Northern blotting or primer extension, or indirectly by measuring the amount of gene product expressed from the promoter.

"Transcription" means according to the invention the process by which a complementary RNA molecule is produced starting from a DNA template. Proteins such-as RNA polymerase, so-called sigma factors and transcriptional regulator proteins are involved in this process. The synthesized RNA then serves as template in the translation process which then leads to the biosynthetically active protein.

A "functional linkage" means in this connection, for example, the sequential arrangement of one of the promoters of the invention and of a nucleic acid sequence to be expressed and, if appropriate, further regulatory elements such as, for example, a terminator in such a way that each of the regulatory elements is able to fulfil its function in the expression of the nucleic acid sequence. A direct linkage in the chemical sense is not absolutely necessary for this. Genetic control sequences such as, for example, enhancer sequences can also carry out their function on the target sequence from more remote positions or even from other DNA molecules. Arrangements in which the nucleic acid sequence to be expressed or the gene to be expressed is positioned behind (i.e., at the 3' end) of the promoter sequence of the invention, so that the two sequences are covalently connected together, are preferred. The distance between the promoter sequence and the nucleic acid sequence to be expressed can be, for example, less than 200 base pairs, fewer than 100 base pairs, or fewer than 50 base pairs.

An "expression activity" or "expression rate" means the amount of protein produced during a set period of time. In the present invention, the protein is encoded by a gene which is functionally linked to with either the HSP promoter or the HYP promoter.

A "caused expression activity" or "caused expression rate" means the amount of protein produced during a set period of time when such protein is caused to be produced. In the present invention, a protein is caused to be produced when the gene encoding the protein is functionally linked to with either the HSP promoter or the HYP promoter, but is not produced in noticeable amount when these promoters are not functionally linked to the gene.

The formation rate at which a biosynthetically active protein/enzyme is produced is a product of the rate of transcription and of translation. It is possible according to the invention to influence both rates, and thus to influence the rate of formation of products in a microorganism.

"Heterologous" gene expression means according to the invention that the promoter and the gene functionally linked thereto do not naturally occur in this arrangement in a wild-type organism. Heterologous gene expression thus comprises the cases where the promoter or the gene to be expressed or both components do not occur naturally in the wild type of the corresponding organism, or else where both promoter and the gene to be expressed are naturally present in the wild-type organism but are on remote chromosomal positions, so that no functional linkage is present in the wild-type organism.

The term "wild type" or "wild-type organism" means according to the invention the corresponding initial organism.

Depending on the context, the term "organism" may mean the initial organism (wild type) or a genetically modified organism of the invention, for example an organism of the genus *Yarrowia*.

The term "substitution" means the exchange of one or more nucleotides for one or more nucleotides. "Deletion" is the replacement of a nucleotide by a direct linkage. Insertions are introductions of nucleotides into the nucleic acid sequence, where there is formal replacement of a direct linkage by one or more nucleotides.

Identity between two nucleic acids means the identity of the nucleotides over the whole length of the nucleic acid in each case, especially the identity calculated by comparison with the aid of the Vector NTI Suite 7.1 software from Informax (USA) using the Clustal method (Higgins D G, Sharp P M., (1998) Fast and sensitive multiple sequence alignments on a microcomputer. Comput Appl. Biosci. 5(2): 151-1) setting the following parameters:

Multiple Alignment Parameter:
Gap opening penalty 10
Gap extension penalty 10
Gap separation penalty range 8
Gap separation penalty off
% identity for alignment delay 40
Residue specific gaps off
Hydrophilic residue gap off
Transition weighing 0
Pairwise Alignment Parameter:
FAST algorithm on
K-tuple size 1
Gap penalty 3
Window size 5
Number of best diagonals 5

For example, a nucleic acid sequence having an identity of at least 70% with the sequence SEQ ID NO: 1 or 2 accordingly means a nucleic acid sequence which, on comparison of its sequence with the sequence SEQ ID NO: 1 or 2, in particular-in accordance with the above programming algorithm with the above set of parameters, shows an identity of at least 70%.

"Hybridization" means the ability of a poly- or oligonucleotide to bind under stringent conditions to an almost complementary sequence, while nonspecific bindings between non-complementary partners do not occur under these conditions. For this, the sequences should preferably be 90-100% complementary. The property of complementary sequences being able to bind specifically to one another is made use of for example in the Northern or Southern blotting technique or in primer binding in PCR or RT-PCR.

The hybridization takes place according to the invention under stringent conditions. Such hybridization conditions are described for example in Sambrook, J., Fritsch, E. F., Maniatis, T., in: Molecular Cloning (A Laboratory Manual), 2nd edition, Cold Spring Harbor Laboratory Press, 1989, pages 9.31-9.57, or in Current Protocols in Molecular Biology, John Wiley & Sons, N.Y. (1989), 6.3.1-6.3.6.

Stringent hybridization conditions mean in particular: Overnight incubation at 42° C. in a solution consisting of 50% formamide, 5×SSC (750 mM NaCl, 75 mM trisodium citrate), 50 mM sodium phosphate (pH 7.6), 5×Denhardt's solution, 10% dextran sulfate and 20 g/ml denatured, sheared salmon sperm DNA, followed by washing the filters with 0.1×SSC at 65° C.

A "functionally equivalent fragment" means for promoters fragments which have essentially the same promoter activity as the initial sequence.

"Fragments" mean partial sequences of the promoters described in the application.

It is particularly preferred to use the nucleic acid sequence SEQ ID NO:1 or SEQ ID NO:2 as promoter for expressing genes in organisms of the genus *Yarrowia*.

All the aforementioned promoters can further be produced in a manner known per se by chemical synthesis from the nucleotide building blocks, such as, for example, by fragment condensation of individual overlapping, complementary nucleic acid building blocks of the double helix. The chemical synthesis of oligonucleotides can take place for example in a known manner by the phosphoamidite method (Voet, Voet, (1995) Biochemistry, 2nd edition, Wiley Press New York, pp. 896-897). Addition of synthetic oligonucleotides and filling in of gaps using the Klenow fragment of DNA polymerase and ligation reactions, and general cloning methods are described in Sambrook et al. (1989) Molecular cloning: A laboratory manual, Cold Spring Harbor Laboratory Press.

It is possible with the promoters of the invention in principle for any gene to be expressed, in organisms of the genus *Yarrowia*. These genes to be expressed in organisms of the genus *Yarrowia* are also called "effect genes" hereinafter.

Preferred effect genes are genes from biosynthetic pathways of biosynthetic products which can be produced in organisms of the genus *Yarrowia*, i.e., in the wild type or by genetic alteration of the wild type.

Preferred biosynthetic products are fine chemicals. The term "fine chemical" is known in the art and includes compounds which are produced by an organism and are used in various branches of industry such as, for example but not limited to, the pharmaceutical industry, the agriculture, cosmetics, food and feed industries. These compounds include organic acids such as, for example, tartaric acid, itaconic acid and diaminopimelic acid, lipids, saturated and unsaturated fatty acids (e.g., arachidonic acid), diols (e.g., propanediol and butanediol), aromatic compounds (e.g., aromatic amines, vanillin and indigo), carotenoids and vitamins and cofactors.

Higher animals have lost the ability to synthesize vitamins, carotenoids, cofactors and nutraceuticals and therefore need to take them in, although they are easily synthesized by other organisms such as bacteria. These molecules are either biologically active molecules per se or precursors of biologically active substances which serve as electron carriers or intermediates in a number of metabolic pathways. These compounds have, besides their nutritional value, also a significant industrial value as coloring agents, antioxidants and catalysts or other processing aids. The term "vitamin" is known in the art and includes nutrients which are required by an organism for normal functioning, but cannot be synthesized by this organism itself. The group of vitamins may include cofactors and nutraceutical compounds. The term "cofactor" includes non-protein compounds which are necessary for the occurrence of normal enzymatic activity. These compounds may be organic or inorganic; the cofactor molecules of the invention are preferably organic. The term "nutraceutical" includes food additives which promote health in organisms and animals, especially in humans. Examples of such molecules are vitamins, antioxidants and likewise certain lipids (e.g., polyunsaturated fatty acids).

Preferred fine chemicals or biosynthetic products which can be produced in organisms of the genus *Yarrowia* are carotenoids such as, for example, phytoene, lycopene, beta-carotene, lutein, zeaxanthin, astaxanthin, canthaxanthin, echinenone, 3-hydroxyechinenone, 3'-hydroxyechinenone, adonirubin, violaxanthin and adonixanthin.

Preferred carotenoids are ketocarotenoids such as, for example, astaxanthin, canthaxanthin, echinenone, 3-hydroxyechinenone, 3'-hydroxyechinenone, adonirubin and adonixanthin.

Preferred genes expressed with the promoters of the invention in yeast are accordingly genes selected from the group of nucleic acids encoding a protein from: a) the biosynthetic pathway of organic acids, b) the biosynthetic pathway of lipids and fatty acids, c) the biosynthetic pathway of diols, d) the biosynthetic pathway of aromatic compounds, e) the biosynthetic pathway of vitamins, or f) the biosynthetic pathway of carotenoids, especially ketocarotenoids.

Preferred genes expressed with the promoters of the invention in organisms of the genus *Yarrowia* are accordingly genes which encode proteins from the biosynthetic pathway of carotenoids.

Preferred genes are selected from the group of nucleic acids encoding a ketolase, nucleic acids encoding a [beta]-hydroxylase, nucleic acids encoding a [beta]-cyclase, nucleic acids encoding an [epsilon]-cyclase, nucleic acids encoding a zeaxanthin epoxidase, nucleic acids encoding an antheraxanthin epoxidase, nucleic acids encoding a neoxanthin synthase, nucleic acids encoding an HMG-CoA reductase, nucleic acids encoding an (E)-4-hydroxy-3-methylbut-2-enyl-diphosphate reductase, nucleic acids encoding a 1-deoxy-D-xylose-5-phosphate synthase, nucleic acids encoding a 1-deoxy-D-xylose-5-phosphate reductoisomerase, nucleic acids encoding an isopentenyl-diphosphate [Delta]-isomerase, nucleic acids encoding a geranyl-diphosphate synthase, nucleic acids encoding a farnesyl-diphosphate synthase, nucleic acids encoding a geranyl-geranyl-diphosphate synthase, nucleic acids encoding a phytoene synthase, nucleic acids encoding a phytoene desaturase (phytoene dehydrogenase), nucleic acids encoding a prephytoene synthase, nucleic acids encoding a zeta-carotene desaturase, nucleic acids encoding a crtISO protein, nucleic acids encoding a 4-diphosphocytidyl-2-C-methyl-D-erythritol synthase, nucleic acids encoding a 4-diphosphocytidyl-2-C-methyl-D-erythritol kinase, nucleic acids encoding a 2-methyl-D-erythritol-2,4-cyclodiphosphate synthase and nucleic acids encoding a hydroxymethylbutenyl-diphosphate synthase.

A ketolase means a protein which has the enzymatic activity of introducing a keto group on the optionally substituted [beta]-ionone ring of carotenoids. Ketolase means in particular a protein which has the enzymatic activity of converting [beta]-carotene into canthaxanthin. Examples of nucleic acids encoding a ketolase, and the corresponding ketolases, are for example sequences from *Haematococcus pluvialis*, especially from *Haematococcus pluvialis Haematococcus pluvialis, Agrobacterium aurantiacum, Alicaligenes, Paracoccus marcusii, Synechocystis, Bradyrhizobium, Haematococcus pluvialis, Paracoccus, Brevundimonas aurantiaca, Nodularia spumigena.*

A [beta]-cyclase means a protein which has the enzymatic activity of converting a terminal linear lycopene residue into a [beta]-ionone ring. A [beta]-cyclase means in particular a protein which has the enzymatic activity of converting [gamma]-carotene into [beta]-carotene. Examples of [beta]-cyclase genes are nucleic acids encoding [beta]-cyclases of the following Accession Numbers: 566350 lycopene beta-cyclase, CAA60119 lycopene synthase, AAG10429 beta cyclase [*Yarrowia erecta*], AAA81880 lycopene cyclase, AAB53337 Lycopene beta cyclase, AAL92175 beta-lycopene cyclase [*Sandersonia aurantiaca*], CAA67331 lycopene cyclase [*Narcissus pseudonarcissus*], AAM45381 beta cyclase [*Yarrowia erecta*], AAL01999 lycopene cyclase [*Xanthobacter* sp. Py2], ZP_000190 hypothetical protein [*Chloroflexus aurantiacus*], AAF78200 lycopene cyclase [*Bradyrhizobium* sp. ORS278], BAB79602 crtY [*Pantoea*

*agglomerans* pv. *milletiae*], CAA64855 lycopene cyclase [*Streptomyces griseus*], AAA21262 dycopene cyclase [*Pantoea agglomerans*], C37802 crtY protein—*Erwinia uredovora*, BAB79602 crtY [*Pantoea agglomerans* pv. *milletiae*], AAA64980 lycopene cyclase [*Pantoea agglomerans*], AAC44851 lycopene cyclase, BAA09593 Lycopene cyclase [*Paracoccus* sp. MBIC1143], CAB56061 lycopene beta-cyclase [*Paracoccus marcusii*], BAA20275 lycopene cyclase [*Erythrobacter longus*], AAK07430 lycopene beta-cyclase [*Adonis palaestina*], CAA67331 lycopene cyclase [*Narcissus pseudonarcissus*], AAB53337 Lycopene beta cyclase, BAC77673 lycopene beta-monocyclase [marine bacterium P99-3].

A hydroxylase means a protein which has the enzymatic activity of introducing a hydroxy group on the optionally substituted [beta]-ionone ring of carotenoids. A hydroxylase means in particular a protein which has the enzymatic activity of converting [beta]-carotene into zeaxanthin or canthaxanthin into astaxanthin. Examples of a hydroxylase gene are: a nucleic acid encoding a hydroxylase from *Haematococcus pluvialis*, Accession AX038729, WO 0061764); and hydroxylases of the following Accession Numbers: CAA70427.1, CAA70888.1, CAB55625.1, AF499108-1, AF315289-1, AF296158-1, AAC49443.1, NP-194300.1, NP-200070.1, AAG10430.1, CAC06712.1, AAM88619.1, CAC95130.11 AAL80006.1, AF162276-1, AA053295.1, MN85601.1, CRTZ_ERWHE, CRTZ_PANAN, BAB79605.1, CRTZ_ALCSP, CRTZ_AGRAU, CAB56060.1, ZP-00094836.1, AAC44852.1, BAC77670.1, NP-745389.1, NP-344225.1, NP-849490.1 ZP-00087019.1, NP-503072.1, NP-852012.1, NP-115929.1, ZP-00013255.1.

An HMG-CoA reductase means a protein which has the enzymatic activity of converting 3-hydroxy-3-methylglutaryl-coenzyme A into mevalonate.

An (E)-4-hydroxy-3-methylbut-2-enyl-diphosphate reductase means a protein which has the enzymatic activity of converting (E)4-hydroxy-3-methylbut-2-enyl diphosphate into isopentenyl diphosphate and dimethylallyl diphosphates.

A 1-deoxy-D-xylose-5-phosphate synthase means a protein which has the enzymatic activity of converting hydroxyethyl-ThPP and glyceraldehyde 3-phosphate into 1-deoxy-D-xylose 5-phosphate:

A 1-deoxy-D-xylose-5-phosphate reductoisomerase means a protein which has the enzymatic activity of converting 1-deoxy-D-xylose 5-phosphate into 2-C-methyl-D-erythritol 4-phosphate.

An isopentenyl-diphosphate [Delta]-isomerase means a protein which has the enzymatic activity of converting isopentenyl diphosphate into dimethylallyl phosphate.

A geranyl-diphosphate synthase means a protein which has the enzymatic activity of converting isopentenyl diphosphate and dimethylallyl phosphate into geranyl diphosphate.

A farnesyl-diphosphate synthase means a protein which has the enzymatic activity of sequentially converting 2 molecules of isopentenyl diphosphate with dimethylallyl diphosphate and the resulting geranyl diphosphate into farnesyl diphosphate.

A geranyl-geranyl-diphosphate synthase means a protein which has the enzymatic activity of converting farnesyl diphosphate and isopentenyl diphosphate into geranyl-geranyl diphosphate.

A phytoene synthase means a protein which has the enzymatic activity of converting geranyl-geranyl diphosphate into phytoene.

A phytoene desaturase means a protein which has the enzymatic activity of converting phytoene into phytofluene and/or phytofluene into 4-carotene (zeta-carotene).

A zeta-carotene desaturase means a protein which has the enzymatic activity of converting [zeta]-carotene into neurosporin and/or neurosporin into lycopene. A crtISO protein means a protein which has the enzymatic activity of converting 7,9,7',9'-tetra-cis-lycopene into all-trans-lycopene.

Examples of HMG-CoA reductase genes are: A nucleic acid encoding an HMG-CoA reductase from *Arabidopsis thaliana*, Accession NM-106299; and further HMG-CoA reductase genes from other organisms with the following Accession Numbers: P54961, P54870, P54868, P54869, O02734, P22791, P54873, P54871, P23228, P13704, P54872, Q01581, P17425, P54874, P54839, P14891, P34135, O64966, P29057, P48019, P48020, P12683, P43256, Q9XEL8, P34136, O64967, P29058, P48022, Q41437, P12684, Q00583, Q9XHL5, Q41438, Q9YAS4, O76819, O28538, Q9Y7D2, P54960, O51628, P48021, Q03163, P00347, P14773, Q12577, Q59468, P04035, O24594, P09610, Q58116, O26662, Q01237, O01559, Q12649, O74164, O59469, P51639, O10283, O08424, P20715, P13703, P13702, Q96UG4, Q8SQZ9, O15888, Q9TUM4, P93514, Q39628, P93081, P93080, Q944T9, Q40148, Q84MM0, Q84LS3, Q9Z9N4, Q9KLM0.

Examples of (E)-4-hydroxy-3-methylbut-2-enyl-diphosphate reductase genes are: A nucleic acid encoding an (E)-4-hydroxy-3-methylbut-2-enyl-diphosphate reductase from *Arabidopsis thaliana* (lytB/ISPH) and further (E)-4-hydroxy-3-methylbut-2-enyl-diphosphate reductase genes from other organisms with the following Accession Numbers: T04781, AF270978-1, NP-485028.1, NP-442089.1, NP-681832.1, ZP-00110421.1, ZP-00071594.1, ZP-00114706.1, ISPH_SYNY3, ZP-00114087.1, ZP-00104269.1, AF398145-1, AF398146-1, AAD55762.1, AF514843-1, NP-622970.1, NP-348471.1, NP-562001.1, NP-223698.1, NP-781941.1, ZP-00080042.1, NP-859669.1, NP-214191.1, ZP-00086191.1, ISPH_VIBCH, NP-230334.1, NP-742768.1, NP-302306.1, ISPH_MYCLE, NP-602581.1, ZP-00026966.1, NP-520563.1, NP-253247.1, NP-282047.1 ZP-00038210.1, ZP-00064913.1, CAA61555.1, ZP-00125365.1, ISPH_ACICA, EAA24703.1, ZP-00013067.1, ZP-00029164.1, NP-790656.1, NP-217899.1, NP-641592.1, NP-636532.1, NP-719076.1, NP-660497.1, NP-422155.1, NP-715446.1, ZP-00090692.1, NP-759496.1, ISPH BURPS, ZP-00129657.1, NP-215626.1, NP-335584.1, ZP-00135016.1, NP-789585.1, NP-787770.1, NP-769647.1, ZP-00043336.1, NP-242248.1, ZP-00008555.1, NP-246603.1, ZP-00030951.1, NP-670994.1, NP-404120.1, NP-540376.1, NP-733653.1, NP-697503.1, NP-840730.1, NP-274828.1, NP-796916.1, ZP-00123390.1, NP-824386.1, NP-737689.1, ZP-00021222.1, NP-757521.1, NP-390395.1, ZP-00133322.1, CAD76178.15 NP-600249.1, NP-454660.1, NP-712601.1, NP-385018.1, NP-751989.1.

Examples of 1-deoxy-D-xylose-5-phosphate synthase genes are: A nucleic acid encoding a 1-deoxy-D-xylose-5-phosphate synthase from *Lycopersicon esculentum*, and further 1-deoxy-D-xylose-5-phosphate synthase genes from other organisms with the following Accession Numbers: AF143812-1, DXS_CAPAN, CAD22530.1, AF182286-1, NP-193291.1, T52289, AAC49368.1, AAP14353.1, D71420, DXS_ORYSA, AF443590-1, BAB02345.1, CAA09804.2, NP-850620.1, CAD22155.2, AAM65798.1, NP-566686.1; CAD22531.1, AAC33513.1, CAC08458.1, AAG10432.1, T08140, AAP14354.1, AF428463-1, ZP-00010537.1, NP-769291.1, AAK59424.1, NP-107784.1, NP-697464.1, NP-540415.1, NP-196699.1, NP-384986.1, ZP-00096461.1, ZP-00013656.1, NP-353769.1, BAA83576.1, ZP-00005919.1, ZP-00006273.1, NP-420871.1, AAM48660.1, DXS_RHOCA, ZP-00045608.1, ZP-00031686.1, NP-841218.1, ZP-00022174.1, ZP-00086851.1, NP-742690.1, NP-520342.1, ZP-00082120.1, NP-790545.1, ZP-00125266.1, CAC17468.1, NP-252733.1, ZP-00092466.1, NP-439591.1, NP-414954.1, NP-752465.1, NP-622918.1, NP-286162.1, NP-836085.1, NP-706308.1, ZP-00081148.1, NP-797065.1, NP-213598.1, NP-245469.1, ZP-00075029.1, NP-455016.1, NP-230536.1, NP-459417.1, NP-274863.1, NP-283402.1, NP-759318.1, NP-406652.1, DXS_SYNLE, DXS_SYNP7, NP-440409.1, ZP-00067331.1, ZP-00122853.17 NP-717142.1, ZP-00104889.1, NP-243645.1, NP-681412.1, DXS_SYNEL, NP-637787.1, DXS-CHLTE, ZP-00129863.1, NP-661241.1, DXS_XANCP, NP-470738.1, NP-484643.1, ZP-00108360.1, NP-833890.1, NP-846629.1, NP-658213.1, NP-642879.1, ZP-00039479.1, ZP-00060584.1, ZP-00041364.1, ZP-00117779.1, NP-299528.1.

Examples of 1-deoxy-D-xylose-5-phosphate reductoisomerase genes are: A nucleic acid encoding a 1-deoxy-D-xylose-5-phosphate reductoisomerase from *Arabidopsis thaliana* and further 1-deoxy-D-xylose-5-phosphate reductoisomerase genes from other organisms with the following Accession Numbers: AF148852, AY084775, AY054682, AY050802, AY045634, AY081453, AY091405, AY098952, AJ242588, AB009053, AY202991, NP-201085.1, T52570, AF331705-1, BAB16915.1, AF367205-1, AF250235-1, CAC03581.1, CAD22156.1, AF182287-1, DXR_M ENPI, ZP-00071219.1, NP-488391.1, ZP-00111307.1, DXR_SYNLE, AAP56260.1, NP-681831.1, NP-442113.1, ZP-00115071.1, ZP-00105106.1, ZP-00113484.1, NP-833540.1, NP-657789.1, NP-661031.1, DXR-BACHD, NP-833080.1, NP-845693.1, NP-562610.1, NP-623020.1, NP-810915.1, NP-243287.1, ZP-00118743.1, NP-464842.1, NP-470690.1, ZP-00082201.1, NP-781898.1, ZP-00123667.1, NP-348420.1, NP-604221.1, ZP-00053349.1, ZP-00064941.1, NP-246927.1, NP-389537.1, ZP-00102576.15 NP-519531.1, AF124757-19, DXR_ZYMMO, NP-713472.1, NP-459225.1, NP-454827.1, ZP-00045738.1, NP-743754.1, DXR_PSEPK, ZP-00130352.1, NP-702530.1, NP-8417441, NP-438967.1, AF514841-1, NP-706118.1, ZP-00125845.1, NP-404661.1, NP-285867.1, NP-240064.1, NP-414715.1, ZP-00094058.1, NP-791365.1, ZP-00012448.1, ZP-00015132.1, ZP-00091545.1, NP-629822.1, NP-771495.1, NP-798691.1, NP-231885.1, NP-252340.1, ZP-00022353.1, NP-355549.1, NP-420724.1, ZP-00085169.1, EAA17616.1, NP-273242.1, NP-219574.1 NP-387094.1, NP-296721.1, ZP-00004209.1, NP-823739.1, NP-282934.1, BAA77848.1, NP-660577.1, NP-760741.1, NP-641750.1, NP-636741.1, NP-829309.1, NP-298338.1, NP-444964.1, NP-717246.1, NP-224545.1, ZP-00038451.1, DXR_KITGR, NP-778563.1.

Examples of isopentenyl-diphosphate [Delta]-isomerase genes are: A nucleic acid encoding an isopentyl-diphosphate [Delta]-isomerase from *Adonis palaestina* and further isopentenyl-diphosphate [Delta]-isomerase genes from other organisms with the following Accession Numbers: Q38929, O48964, Q39472, Q13907, O35586, P58044, O42641, 035760, Q10132, P15496, Q9YB30, Q8YNH4, Q42553, O27997, P50740, O51627, O48965, Q8KFR5, Q39471, Q39664, Q9RVE2, Q01335, Q9HHE4, Q9BXS1, Q9KWF6, Q9CIF5, Q88WB6, Q92BX2, Q8Y7A5, Q8TT35 Q9KK75, Q8NN99, Q8XD58, Q7FE75, Q46822, Q9HP40, P72002, P26173, Q9Z5D3, Q8Z3X9, Q8ZM82, Q9X7Q6, O13504, Q9HFW8, Q8NJL9, Q9UUQ1, Q9NH02, Q9M6K9, Q9M6K5, Q9FXR6, O081691, Q9S7C4, Q8S3L8, Q9M592, Q9M6K3, Q9M6K7, Q9FV48, Q9LLB6, Q9AVJ1, Q9AVG8, Q9M6K6, Q9AVJ5, Q9M6K2, Q9AYS5, Q9M6K8, Q9AVG7, Q8S3L7, Q8W250, Q941E1, Q9AVI8, Q9AYS6, Q9SAY0, Q9M6K4, Q8GVZ0, Q84RZ8, Q8KZ12, Q8KZ66, Q8FND7, Q88QC9, Q8BFZ6, BAC26382, CAD94476.

Examples of geranyl-diphosphate synthase genes are: A nucleic acid encoding a geranyl-diphosphate synthase from *Arabidopsis thaliana* and further geranyl-diphosphate synthase genes from other organisms with the following Accession Numbers: Q9FT89, Q8LKJ2, Q9FSW8, Q8LKJ3, Q9SBR3, Q9SBR4, Q9FET8, Q7LKJ1, Q84LG1, Q9JK86.

Examples of farnesyl-diphosphate synthase genes are: A nucleic acid encoding a farnesyl-diphosphate synthase from *Arabidopsis thaliana* and further farnesyl-diphosphate synthase genes from other organisms with the following Accession Numbers: P53799, P37268, Q02769, Q09152, P49351, O24241, Q43315, P49352, O24242, P49350, P08836, P14324, P49349, P08524, O66952, Q082911 P54383, Q45220, P57537, Q8K9A0, P22939, P45204, O66126, P55539, Q9SWH9, Q9AVI7, Q9FRX2, Q9AYS7, Q94IE8, Q9FXR9, Q9ZWF6, Q9FXR8, Q9AR37, O50009, Q94IE9, Q8RVK7, Q8RVQ7, O04882, Q93RA8, Q93RB0, Q93KB4, Q93RB5, Q93RB3, O93RB1, Q93RB2, Q920E5. Examples of geranyl-geranyl-diphosphate synthase genes are: A nucleic acid encoding a geranyl-geranyl-diphosphate synthase from *Sinapis alba* and further geranyl-geranyl-diphosphate synthase genes from other organisms.

Examples of phytoene synthase genes are: A nucleic acid encoding a phytoene synthase from *Erwinia uredovora* and further phytoene synthase genes from other organisms. Examples of phytoene desaturase genes are: A nucleic acid encoding a phytoene desaturase from *Erwinia uredovora* and further phytoene desaturase genes from other organisms. Examples of zeta-carotene desaturase genes are: A nucleic acid encoding a zeta-carotene desaturase from *Narcissus pseudonarcissus* and further zeta-carotene desaturase genes from other organisms.

Examples of crtISO genes are: A nucleic acid encoding a crtISO from *Lycopersicon esculentum* and further crtISO genes from other organisms.

The invention further relates to a genetically modified microorganism of the genus *Yarrowia*, where the genetic modification leads to an increased expression rate or caused expression of at least one gene compared with the wild type and the expression is caused by the promoters described in the invention.

In a preferred embodiment of the genetically modified organisms of the invention of the genus *Yarrowia*, the regulation of the expression of genes in the organism by the promoters of the invention is achieved by:

a) introducing one or more of the above-mentioned recombinant nucleic acid molecule into the genome of said microorganism, so that the expression of one or more endogenous genes of said microorganism takes place under the control of the introduced recombinant nucleic acid molecule;
b) introducing one or more genes into the genome of said microorganism, so that the expression of one or more of the introduced genes takes place under the control of the above-mentioned recombinant nucleic acid molecule which is endogenous to said microorganism; or c) introducing one or more nucleic acid constructs into said microorganism, wherein said one or more nucleic acid constructs comprise at least one of the above-mentioned recombinant nucleic acid molecule and this one or more recombinant nucleic acid molecule is functionally linked to one or more genes to be expressed.

In one embodiment, integration of the nucleic acid constructs in the microorganism of the genus *Yarrowia* according to feature c) can take place intrachromosomally or extrachromosomally.

Preferred promoters of the invention and preferred genes to be expressed (effect genes) are described above.

The production of the genetically modified microorganisms of the genus *Yarrowia* with increased or caused expression rate of an effect gene is described by way of example below.

The transformation can in the case of combinations of genetic modifications take place singly or by multiple constructs.

The transgenic organisms are preferably produced by transformation of the initial organisms with a nucleic acid construct which comprises at least one of the promoters of the invention described above which are functionally linked to an effect gene to be expressed and, if appropriate, further regulatory signals.

These nucleic acid constructs in which the promoters of the invention and effect genes are functionally linked are also called expression cassettes hereinafter.

The expression cassettes may comprise further regulatory signals that are regulatory nucleic acid sequences which control the expression of the effect genes in the host cell. In a preferred embodiment, an expression cassette comprises at least one promoter of the invention upstream, i.e., at the 5' end of the coding sequence, and a polyadenylation signal and, if appropriate, further regulatory elements which are operatively linked to the coding sequence, lying in between, of the effect gene for at least one of the genes described above, downstream, i.e., at the 3' end.

An operative linkage means the sequential arrangement of promoter, coding sequence, terminator and, if appropriate, further regulatory elements in such a way that each of the regulatory elements can complete its function as intended in the expression of the coding sequence.

The preferred nucleic acid constructs, expression cassettes and vectors for organisms and processes for producing transgenic organisms, and the transgenic organisms of the genus *Yarrowia* themselves, are described in WO2006/102342 and by way of example below.

The nucleic acids of the invention can be produced by synthesis or be obtained naturally or comprise a mixture of synthetic and natural nucleic acid constituents, and consist of various heterologous gene segments from different organisms.

Preference is given, as described above, to synthetic nucleotide sequences with codons preferred by organisms. These codons preferred by organisms can be determined from codons with the highest protein frequency which are expressed in most of the organism species of interest.

It is possible in the preparation of an expression cassette to manipulate various DNA fragments in order to obtain a nucleotide sequence which expediently reads in the correct direction and which is equipped with a correct reading frame. Adaptors or linkers can be attached to the fragments to join the DNA fragments together.

It is expediently possible for the promoter and terminator regions to be provided, in the direction of transcription, with a linker or polylinker comprising one or more restriction sites for inserting this sequence. Ordinarily, the linker has 1 to 10, in most cases 1 to 8, preferably 2 to 6, restriction sites. In general, the linker within the regulatory regions has a size of less than 100 bp, frequently less than 60 bp, but at least 5 bp. The promoter can be both native, or homologous, and foreign, or heterologous, with regard to the host organism. The expression cassette preferably comprises, in the 5'-3' direction of transcription, the promoter, a coding nucleic acid sequence or a nucleic acid construct and a region for termination of transcription. Different termination regions can be mutually exchanged as desired.

Particularly preferred effect genes are those selected from the group of nucleic acids encoding a ketolase, nucleic acids encoding a [beta]-hydroxylase, nucleic acids encoding a [beta]-cyclase, nucleic acids encoding an [epsilon]-cyclase, nucleic acids encoding an epoxidase, nucleic acids encoding an HMG-CoA reductase, nucleic acids encoding an (E)-4-hydroxy-3-methylbut-2-enyl-diphosphate reductase, nucleic acids encoding a 1-deoxy-D-xylose-5-phosphate synthase, nucleic acids encoding a 1-deoxy-D-xylose-5-phosphate reductoisomerase, nucleic acids encoding an isopentenyl-diphosphate [Delta]-isomerase, nucleic acids encoding a geranyl-diphosphate synthase, nucleic acids encoding a farnesyl-diphosphate synthase, nucleic acids encoding a geranyl-geranyl-diphosphate synthase, nucleic acids encoding a phytoene synthase, nucleic acids encoding a phytoene desaturase, nucleic acids encoding a prephytoene synthase and nucleic acids encoding a zeta-carotene desaturase.

It is possible with the aid of the processes of the invention described above to regulate through the promoters of the invention the metabolic pathways to specific biosynthetic products in the genetically modified organisms of the invention described above of the genus *Yarrowia*.

For this purpose, for example, metabolic pathways which lead to a specific biosynthetic product are enhanced by causing or increasing the transcription rate or expression rate of genes of this biosynthetic pathway through the increased amount of enzyme leading to an increased total activity of these enzymes of the desired biosynthetic pathway and thus to an enhanced metabolic flux toward the desired biosynthetic product.

It is necessary, depending on the desired biosynthetic product, to increase or reduce the transcription rate or expression rate of various genes. It is ordinarily advantageous to alter the transcription rate or expression rate of a plurality of genes, i.e., to increase the transcription rate or expression rate of a combination of genes and/or to reduce the transcription rate or expression rate of a combination of genes.

In the genetically modified organisms of the invention, at least one increased or caused expression rate of a gene is attributable to a promoter of the invention.

Further, additionally altered, i.e., additionally increased or additionally reduced, expression rates of further genes in genetically modified organisms may, but need not, be derived from the promoters of the invention.

The invention therefore relates to a process for producing biosynthetic products by cultivating genetically modified organisms of the invention of the genus *Yarrowia*.

The invention relates in particular to a process for producing carotenoids by cultivating genetically modified organisms of the invention of the genus *Yarrowia*, wherein the genes to be expressed are selected from the group of nucleic acids encoding a ketolase, nucleic acids encoding a [beta]-hydroxylase, nucleic acids encoding a [beta]-cyclase, nucleic acids encoding an [epsilon]-cyclase, nucleic acids encoding an epoxidase, nucleic acids encoding an HMG-CoA reductase, nucleic acids encoding an (E)-4-hydroxy-3-methylbut-2-enyl-diphosphate reductase, nucleic acids encoding a 1-deoxy-D-xylose-5-phosphate synthase, nucleic acids encoding a 1-deoxy-D-xylose-5-phosphate reductoisomerase, nucleic acids encoding an isopentenyl-diphosphate [Delta]-isomerase, nucleic acids encoding a geranyl-diphosphate synthase, nucleic acids encoding a farnesyl-diphosphate synthase, nucleic acids encoding a geranyl-geranyl-diphosphate synthase, nucleic acids encoding a phytoene synthase, nucleic acids encoding a phytoene desaturase, nucleic acids encoding a prephytoene synthase and nucleic acids encoding a zeta-carotene desaturase.

The carotenoids are preferably selected from the group of phytoene, phytofluene, lycopene, lutein, beta-carotene, zeaxanthin, astaxanthin, canthaxanthin, echinenone, 3-hydroxyechinenone, 3'-hydroxyechinenone, adonirubin, violaxanthin and adonixanthin.

The genetically modified organisms can moreover be used to produce extracts containing biosynthetic products, in particular carotenoids, in particular ketocarotenoids, in particular astaxanthin, and/or for producing supplements for animal and human foods, and cosmetics and pharmaceuticals.

The genetically modified organisms of the genus *Yarrowia* have by comparison with the wild type an increased content of the desired biosynthetic products, in particular carotenoids, in particular ketocarotenoids, in particular astaxanthin.

In a preferred embodiment, a yeast promoter of the invention is derived from a *Yarrowia lipolytica* yeast strain.

It is at present contemplated that a yeast promoter of the invention, i.e., an analogous yeast promoter, may be obtained from other micro-organisms. For instance, the yeast promoter may be derived from other yeast strains, such as a strain of *Saccharomyces cerevisiae*.

In another aspect, the invention provides a recombinant expression vector comprising a yeast promoter of the invention.

The expression vector of the invention may be any expression vector that is conveniently subjected to recombinant DNA procedures, and the choice of vector will often depend on the host cell into which it is to be introduced.

The procedures used to ligate a DNA sequence coding for a protein of interest, the yeast promoter and the terminator, respectively, and to insert them into suitable vectors are well known to persons skilled in the art.

In yet another aspect, the invention provides a host cell comprising the recombinant expression vector of the invention.

Preferably, the host cell of the invention is a eukaryotic cell, in particular a yeast cell.

Examples of such yeast host cell include, but are not limited to a strain of *Saccharomyces*, in particular *Saccharomyces cerevisiae, Saccharomyces kluyveri* or *Saccharomyces uvarum*, a strain of *Schizosaccharomyces* sp., such as *Schizosaccharomyces pombe*, a strain of *Hansenula* sp., *Pichia* sp., *Yarrowia* sp., such as *Yarrowia lipolytica*, or *Kluyveromyces* sp., such as *Kluyveromyces lactis*.

In a preferred embodiment, a strain of *Yarrowia lipolytica* is a suitable host for the present invention.

EXAMPLES

The following examples illustrate the invention.

Table 1 below describes certain *Yarrowia lipolytica* strains used in the following exemplification:

TABLE 1

*Yarrowia lipolytica* strains.

| Strain Name | Genotype | Method of Making |
|---|---|---|
| ML2461 | MATA erg9-4789::URA3 tef1P-{HMG-tr GGS carB carRP} prototrophic | Classical and standard molecular genetic techniques |
| ML6804 | MATB erg9-4789::URA3 tef1P-{HMG-tr GGS carB carRP crtW} prototrophic | Classical and standard molecular genetic techniques |
| ML326 | MATA ura3-302 leu2-270 lys8-11 PEX17-HA | ATCC 201249 |

Table 2 below describes certain plasmids used in the following exemplification:

TABLE 2

Plasmids.

| Plasmid | Backbone | Insert |
|---|---|---|
| pMB6056 | pMB6052 ($Hyg^R$ tef1P-xprT) | crtZ |
| pMB6504 | pMB6056 | hspP |
| pMB6509 | pMB6056 | hypP |
| pMB6779 | pMB6149 (LEU2 lacZ) | hspP |
| pMB6781 | pMB6149 | hypP |

*Yarrowia* strains ML2461 and ML6804 were constructed by the introduction of heterologous genes under the control of the endogenous TEF1 promoter (control). The GGS gene and the truncated HMG gene ("HMG-tr") were derived from *Yarrowia* sequences corresponding to native geranyl-geranyl pyrophosphate synthase and hydroxymethylglutaryl-CoA reductase genes, respectively. The carRP and carB genes were derived from *Mucor circinelloides*, and they encode a bifunctional phytoene synthase/lycopene cyclase and a phytoene dehydrogenase, respectively. The crtW gene was synthesized to encode the carotene ketolase of *Parvularcula bermudensis*. The crtZ gene was synthesized to encode the carotene hydroxylase of *Enterobacter pulveris*. These genes are sometimes but not always associated with auxotrophic markers (URA3, LEU2, URA2, LYS1, ADE1) or a loxP site, remnant of a $Hyg^R$ or $Nat^R$ marker.

All basic molecular biology and DNA manipulation procedures described herein are generally performed according to Sambrook et al. or Ausubel et al. (Sambrook J, Fritsch E F, Maniatis T (eds.). 1989. *Molecular Cloning: A Laboratory Manual*. Cold Spring Harbor Laboratory Press: New York; Ausubel F M, Brent R, Kingston R E, Moore D D, Seidman J G, Smith J A, Struhl K (eds). 1998. *Current Protocols in Molecular Biology*. Wiley: New York).

Example 1: Production of pM6504 ($Hyg^R$ HSPp-crtZ), Encoding the HSP Promoter Driving the Carotene Hydroxylase Gene crtZ The sequence specified in SEQ ID No: 1 corresponding to the intragenic region upstream of YALIOD20526g was amplified from gDNA prepared from *Y. lipolytica* ATCC201249, using M08250 [SEQ ID NO 3] (5'-CACACAAAGCTTGGTACCAGATAGTGCAATCACATGTTGCTAC) and M08251 (5'-CACACATTTTGTGGCTAGCATGTAGTATAAGTG TGTGTGTTGG). This fragment was cleaved using NheI and HindI II and ligated to pMB6056 (TEFIp-crtZ HygR) cut with NheI and HindI II to produce pMB6504 (HSPp-crtZ HygR).

Example 2: Production of pMB6509 (Hyg[R] HYPp-crtZ), Encoding the HYP Promoter from *Y. lipolytica* Driving the Carotene Hydroxylase Gene crtZ The sequence specified in SEQ ID N0:2 corresponding to the intragenic region upstream of YALIOD09889g was amplified from gDNA prepared from *Y. lipolytica* ATCC201249, using M08254 [SEQ ID NO 5] (5'-CACACAAAGCTTGGTACCAGATCGCGGTCA-GAAGGGGCAG) and M08255 (5'-CACACATTTGTG-GCTAGCATGTGAGAAAGTAGTTTT GAGATGG). This fragment was cleaved using NheI and HindI II and ligated to pMB6056 (TEFIp-crtZ HygR) cut with NheI and HindI II, to produce pMB6509 (HYPp-crtZ HygR).

Example 3: Zeaxanthin Production pMB6056, pMB6504 and pMB6509 were cleaved with NotI and independently transformed into ML2461, a beta carotene producer, and into ML6804, a canthaxanthin producer. Transformants were selected on YPD supplemented with 100 mg/L hygromycin B. They were incubated for 48 h at 30° C. Colonies were picked to YPD agar supplemented with 100 mg/L hygromycin B.

Cultures of these transformants were grown for 72 h at 30° C. in 800 μL YPD in 2 mL round bottom 24 well plates and shaken at 800 rpm in an INFORS Multitron. For extraction, 250 μL was sampled into 2 mL Eppendorf Safe-Lock™ tubes (022363352). Approximately 600 μL of 0.5 mm dia. Zirconia/Silica beads (BioSpec Products Cat. No. 11079105z) was added to each sample. Cells were disrupted in a Resch MM300 beadmill (setting 20) for 5 min at 4° C. in heptane:ethylacetate (1:1 v:v), and centrifuged for 5 minutes. Multiple rounds of extraction were carried out until the extract was colorless, indicating exhaustion of carotenoids in the sample. Extracts were pooled following disruption, evaporated, resuspended in hexane:ethylacetate (1:1 v:v) and analyzed by HPLC.

FIG. 1 shows carotenoid levels, depicted as HPLC peak area, in ML2461 transformed with HSP or HYP driving crtZ expression in shake flasks. Because insertion in *Yarrowia* is random, chromosomal location varies by transformant. In order to minimize position effects, 10 and 5 transformants were assayed and averaged for HSP and HYP respectively.

Example 4: Astaxanthin Production

Figure 2:
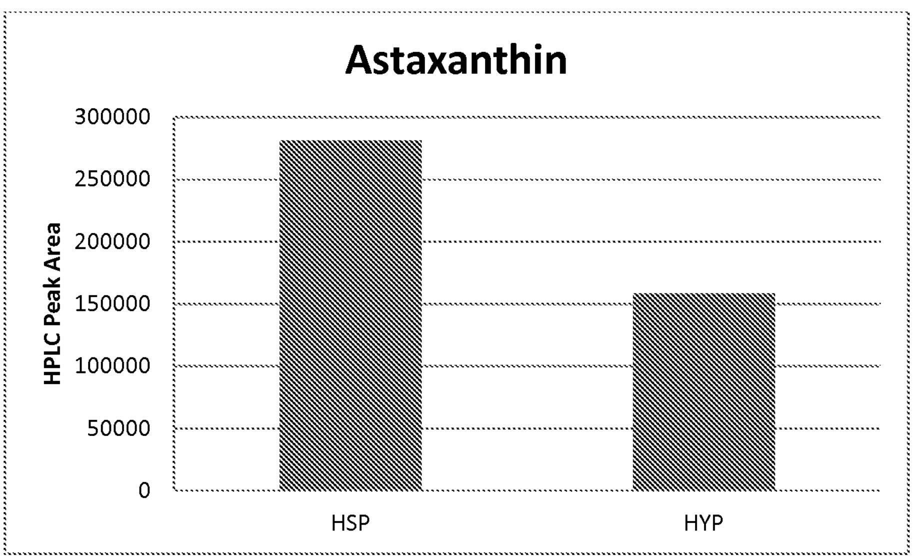

Cultures derived from transformants of ML6804 were grown, sampled and extracted as above. FIG. 2 shows carotenoid levels, depicted as HPLC peak area, in ML6804 transformed with HSP or HYP promoters driving crtZ expression. Average expression of 12 transformants each for HSP and HYP in shake flasks is shown.

Example 5: Gene Expression in Fermentors for Astaxanthin Producers

In order to examine the expression of the above described heterologous constructs under fermentor conditions, the astaxanthin-producing strains created in Example 4 were grown in a fermentor using a fed-batch process conducted in a 3 L bench-scale fermentor. The initial batch phase medium contained 10% soybean oil (vol:vol) as the primary carbon source. During the batch growth phase, biomass level (dry cell weight) reached a maximum, and *Yarrowia* cells accumulated a large internal lipid body. After the initial batch had been consumed, a rapid rise in the fermentor dissolved oxygen level was observed. At that time, a feed of soybean oil was started, with the feed addition rate controlled to maintain the fermentor dissolved oxygen level at 20% of saturation. An aliquot of 25 μL was sampled at time points indicated in FIG. 3 and carotenoids extracted as above. For RNA analysis, fermentors were sampled one at a time to minimize the time from sampling to freezing. Samples were withdrawn and immediately placed on ice. Aliquots were taken in triplicate and centrifuged at 13000 rpm for 45 seconds in 2 mL Eppendorf Safe-Lock™ tubes. The supernatant was discarded and the sample was placed on dry ice until all fermentors were sampled. Samples were stored at −80° C.

RNA was extracted using the Qiagen RNeasy Mini RNA extraction kit (Cat. No. 74106) using the Yeast III protocol with bead beating.

Approximately 600 μL of 0.5 mm diam. Zirconia/Silica beads (BioSpec Products Cat. No. 11079105z) was added to each sample. An aliquot of 600 μL Buffer RLT with β-ME (10 μL β-ME/1 mL RLT) was added to the sample. Cells were disrupted in a Resch MM300 beadmill (setting 20) for 5 min at 4° C. Samples were centrifuged 10 s at top speed and supernatants transferred to a new tube. Samples were re-centrifuged at top speed for 2 min and lysate transferred to a new tube. An aliquot of 350 μL, of 70% ethanol was added to the lysate and mixed by pipetting up and down. An aliquot of 700 μL of the sample was transferred to the RNeasy mini column and centrifuged 15 s at 13000 rpm. The flow-through was discarded. An aliquot of 350 μL Buffer RW1 was added to the column, which was centrifuged 15 s at 13000 rpm. An aliquot of 10 μL, Dnase I stock solution was added to 70 μL of Buffer RDD and mixed by inverting the tube. 80 μL, DNase I solution was added to the RNeasy silica-gel membrane and incubated at room temperature of 15 min. An aliquot of 350 μL, Buffer RW1 was added to the column and it was centrifuged 15 s at 13000 rpm. The flow through was discarded. The RNeasy column was transferred to a new 2 mL collection tube. To wash the column, An aliquot of 500 μL Buffer RPE (with ethanol) was added and it was centrifuged 15 s at 13000 rpm. The flow-through was discarded, and the previous step repeated. The RNeasy column was placed in a new 2 mL collection tube and centrifuged 1 min at 13000 rpm to dry the membrane. The RNeasy column was transferred to a new 1.5 mL collection tube. An aliquot of 50 μL of Rnase-free water was added to the membrane and incubated at room temperature for 1 min. The column was centrifuged at 13000 rpm to elute.

RNA was quantified and tested for quality as above on the Agilent 2100 BioAnalyzer using the Agilent RNA Pico (Agilent #5067-1513) kit.

First strand cDNA was synthesized using the VILO Superscript® Kit (Invitrogen Cat. No. 11754-250) according to the manufacturer's directions. Briefly, 250 ng of RNA was incubated in a 20 μL reaction with 4 μL 5× VILO Reaction Mix, 2 μL 10× SuperScript Enzyme Mix and water. The reaction was incubated at 25° C. for 10 min, 42° C. for 2 h and 85° C. for 5 min. The cDNA was diluted to 0.7 ng/μL prior to qPCR.

Primers for qPCR were designed using the PrimerQuest software freely available on the IDT website, and synthesized by IDT.

TABLE 3

Primers for qPCR.

| Gene | *Yarrowia* ID | Oligo # [SEQ ID NO] | Forward Primer Sequence | Oligo # [SEQ ID NO] | Reverse Primer Sequence |
|---|---|---|---|---|---|
| ACTJ | YALI0D08272g | MO7492 [SEQ ID NO 7] | ACGTTGTGCCC ATCTACTCTGG TT | MO7493 [SEQ ID NO 8] | TCGGCGGAGTTG GTGAAAGAGTA A |
| TEFJ | YALI0009141g | MO7714 [SEQ ID NO 9] | AGTGCGGTGGT ATCGATAAGCG AA | MO7676 [SEQ ID NO 10] | TCTCGCTCAGCC TTAAGCTTGTCA |
| HSP12 | YALI0D20526g | MO8241 [SEQ ID NO 11] | ACATCTCCGAC GAGAAGAACA AGC | MO8242 [SEQ ID NO 12] | AGTTGTTGATGG ACTCCTTGGCCT |
| HYPJ | YALI0D09889g | MO8239 [SEQ ID NO 13] | AGTTTGCCCGA CAGAAGGAGA ACA | MO8240 [SEQ ID NO 14] | ATGGAGTTGAC GGCGAAGATGA GA |
| crtZ | N/A | MO7655 [SEQ ID NO 15] | AGGCTACCTTA AGCGGCTTTAC CA | MO7656 [SEQ ID NO 16] | TTCCGGCTTAGC TGCGTAGAGAA A |

qPCR was performed using the Brilliant III Ultra-Fast SYBER Green® QPCR Master Mix (Agilent Cat. No. 600883) in a Stratagene Mx3000P thermocycler. Several reactions of 20 μL were run. A master mix was set up containing all components except the cDNA, and 15 μL aliquots were added to each reaction along with 5 μL of cDNA. To each reaction was added 10 μL 2× SYBER Mix, 0.3 μL of 500× diluted Reference Dye, 0.7 μL water and 4 μL of primer mix (2 μM each Forward and Reverse Primer). A no reverse transcriptase reaction (NRT) was also run using the ACT1 primer set and 0.7 ng/μL RNA as the template. For each plate, a no template (NTC) reaction was run with 5 μL of water in place of the cDNA. If multiple plates were run for an experiment, an interplate calibrator (IPC) was also included. For the IPC a single template was chosen and run in all plates in triplicate with the ACT1 primer set. All reactions were run in triplicate. ACT1 was chosen to normalize for mRNA amounts and Tef1a, a constitutive housekeeping gene, was used for fold expression calculations.

dCt was calculated to remove variation (Avg Sample−Avg ACT1). ddCt was calculated to normalize to a standard, in this case TEF1a, a strongly expressed endogenous gene. $(2\hat{}(dCt_{Sample}-dCt_{TEF}))$.

Figure 3:
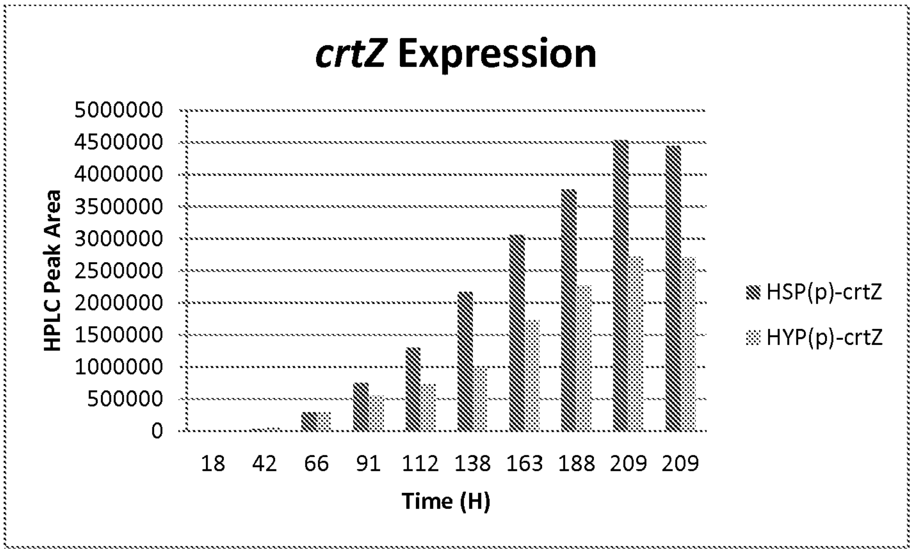
FIG. 3 shows the level of crtZ expression from the two promoters tested in fermentors. The levels are depicted as amounts of astaxanthin produced, as HPLC peak areas, at the different fermentation time points analyzed (y-axis).
Figure 4:
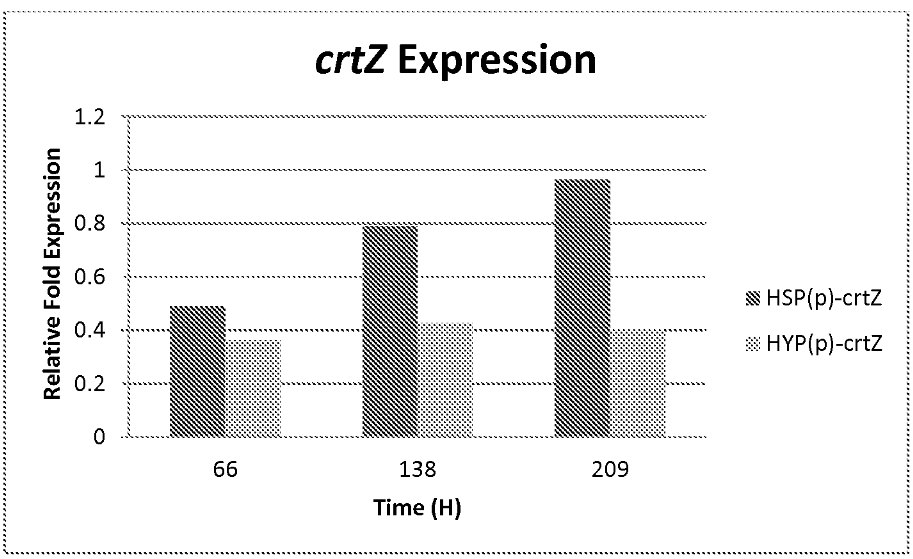
FIG. 4 shows the level of crtZ mRNA expressed in fermentors, relative to a strong constitutively expressed endogenous gene.

FIG. 3 shows the level of crtZ expression as reflected in the levels of astaxanthin produced. FIG. 4 shows relative crtZ RNA expression from the same fermentors as FIG. 3 at three time points.

Example 6: β-Galactosidase Production

In order to assess gene expression from the HYP and the HSP promoters, each promoter was functionally fused to a lacZ reporter gene. Plasmid pMB6149 was cleaved with NheI and HindIII and the appropriate 1 kb NheI-HindIII promoter fragment described in Examples 1 and 2 was inserted to create pMB6779 (HSPp-lacZ) and pMB6781 (HYPp-lacZ). Cultures derived from $Leu^+$ transformants of ML326 were grown in minimal medium overnight supplemented with uracil and lysine, then diluted 1/50 into 10 mL YPD and grown to $2\times10^7$ cells/mL. Cells were pelleted and resuspended in 0.5 mL Breaking Buffer (0.1M Tris pH8, 20% glycerol v/v, 1 mM DTT). An aliquot of 0.25 mL was transferred to fresh tube and 12.5 uL PMSF solution was added (40 mM in 95% ethanol). Zirconia/Silica beads (BioSpec Products Cat No. 11079105z) were added to the meniscus and tubes were vortexed 10 min. Supernatant was transferred to a fresh tube. Solution was centrifuged at max speed at 4° C. for 15 min. An aliquot of 950 μL of Z Buffer (16 g/L $Na_2HPO_4$-$7H_2O$, 5.5 g/L $NaH_2PO_4$—$H_2O$, 0.75 g/L KCl, 0.25 g/L $MgSO_4.7H_2O$, 2.7 mL/L β-mercaptoethanol) and 50 μL extract were combined in a glass tube and placed in a 28° C. water bath. The reactions were started by adding 0.2 mL ONPG Solution (4 mg/mL O-nitrophenyl B-D-galactoside in Z Buffer). Reactions were allowed to proceed until a medium yellow color developed and were stopped by addition of 0.5 mL 1M $Na_4CO_3$. The time was recorded for each reaction and $OD_{420}$ was determined. Total cellular protein was determined by BioRad Protein assay. β-galactosidase units=((OD420)(378)/((time in min)(volume of extract in mL)(protein mg/mL))

Figure 5:
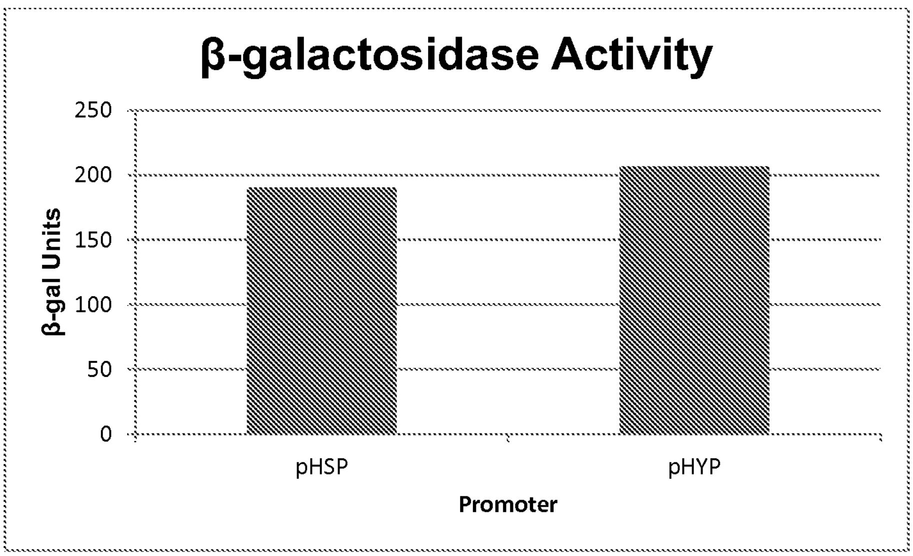
FIG. 5 shows the units of β-galactosidase produced by six different transformants harboring the lacZ gene under the control of the HSP and HYP promoters, respectively.

FIG. 5 shows β-galactosidase production in 4 and 5 strains with HSP or HYP respectively driving expression of a single copy of lacZ in shake flasks.

What may be claimed is:

1. A recombinant nucleic acid molecule comprising a heterologous combination of a first polynucleotide functionally linked to a second polynucleotide encoding a protein, wherein the first polynucleotide comprises a) a polynucleotide sequence having at least 90% identity to the polynucleotide sequence of SEQ ID NO:1 or SEQ ID NO:2, or b) a polynucelotide sequence which hybridizes with the polynucleotide sequence SEQ ID NO:1 or SEQ ID NO:2 under stringent conditions.

2. The recombinant nucleic acid molecule of claim 1, wherein the first polynucleotide comprises a polynucleotide sequence having at least 95% sequence identity to the polynucleotide sequence of SEQ ID NO:1 or SEQ ID NO:2.

3. The recombinant nucleic acid molecule of claim 1 or 2, wherein the first polynucleotide is capable of functioning as a promoter.

4. The recombinant nucleic acid molecule of claim 1 or 2, wherein the first polynucleotide is capable of regulating the expression of the second polynucleotide encoding a protein in yeast.

5. The recombinant nucleic acid molecule of claim 4, wherein said yeast is a strain of *Yarrowia lipolytica*.

6. The recombinant nucleic acid molecule of claim 5, wherein the second polynucleotide encoding a protein is heterologous to an organism of the genus *Yarrowia*.

7. The recombinant nucleic acid molecule of claim 1, wherein the protein is a protein from:

a) the biosynthetic pathway of organic acids, b) the biosynthetic pathway of lipids and fatty acids, c) the biosynthetic pathway of diols, d) the biosynthetic pathway of aromatic compounds, e) the biosynthetic pathway of vitamins, or f) the biosynthetic pathway of carotenoids.

8. The recombinant nucleic acid molecule of claim 1, wherein the recombinant nucleic acid molecule is a vector.

9. A genetically modified microorganism comprising the recombinant nucleic acid molecule of claim 1.

10. The genetically modified microorganism of claim 9, wherein the microorganism is a member of the genus *Yarrowia*.

11. The genetically modified microorganism of claim 10, of the protein is increased as compared with the corresponding wild type microorganism not comprising the recombinant nucleic acid molecule.

12. The genetically modified microorganism of claim 10, wherein a) the first polynucleotide is heterologous to the microorganism and the second polynucleotide is endogenous to the microorganism, and the expression of the second polynucleotide is regulated by the first polynucleotide;

b) the first polynucleotide is endogenous to the microorganism and the second polynucleotide is heterologous to the microorganism, and the expression of the second polynucleotide is regulated by the first polynucleotide; or c) the first polynucleotide and the second polynucleotide are heterologous to the microorganism, and the expression of the second polynucleotide is regulated by the first polynucleotide.

13. A process for production of a biosynthetic product, comprising:

a) cultivating a genetically modified microorganism of the genus *Yarrowia* in a medium, wherein the genetically modified microorganism comprises the recombinant nucleic acid molecule of claim 1; and b) recovering the biosynthetic product made in step a).

14. The process of claim 13, wherein said biosynthetic product is carotenoids.

* * * * *